United States Patent [19]

Mitchell

[11] 4,079,006
[45] Mar. 14, 1978

[54] METHODS OF SCALE INHIBITION
[75] Inventor: Robert S. Mitchell, Webster Groves, Mo.
[73] Assignee: Monsanto Company, St. Louis, Mo.
[21] Appl. No.: 710,931
[22] Filed: Aug. 2, 1976

Related U.S. Application Data

[63] Continuation-in-part of Ser. No. 361,383, May 17, 1973, abandoned.

[51] Int. Cl.² ............................................. C02B 5/06
[52] U.S. Cl. ...................................... 210/58; 252/180; 252/181; 260/502.5; 260/534 R
[58] Field of Search ................... 210/54, 58; 252/180, 252/181; 260/502.5, 534 R

[56] References Cited

U.S. PATENT DOCUMENTS

| | | | |
|---|---|---|---|
| 2,462,008 | 2/1949 | Snider et al. | 260/534 R |
| 3,113,966 | 12/1963 | Formaini et al. | 260/534 R |
| 3,288,846 | 11/1966 | Irani et al. | 260/502.5 |
| 3,476,799 | 11/1969 | Vogt et al. | 260/502.5 |
| 3,505,238 | 4/1970 | Liddell | 252/180 |
| 3,549,728 | 12/1970 | Balde et al. | 260/502.5 |
| 3,563,987 | 2/1971 | Berkowitz | 260/248 A |
| 3,723,347 | 3/1973 | Mitchell | 210/58 |
| 3,751,372 | 8/1973 | Zecher | 210/58 |
| 3,809,654 | 5/1974 | Mitchell | 210/58 |
| 3,890,228 | 6/1975 | Hwa et al. | 210/58 |
| 4,033,896 | 7/1977 | Mitchell et al. | 252/181 |

FOREIGN PATENT DOCUMENTS

| | | | |
|---|---|---|---|
| 1,230,121 | 4/1971 | United Kingdom | 260/502.5 |
| 1,142,294 | 2/1969 | United Kingdom | 260/502.5 |

Primary Examiner—Charles N. Hart
Assistant Examiner—Peter A. Hruskoci
Attorney, Agent, or Firm—F. D. Shearin; E. P. Grattan; S. M. Tarter

[57] ABSTRACT

The precipitation of scale forming salts in an aqueous system is inhibited by adding either stoichiometric or substoichiometric, including threshold, amounts to said system of a phosphonomethylene amino carboxylate of the general formula

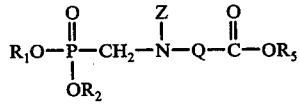

wherein $R_1$, $R_2$, $R_5$, Q and Z are hereinafter defined.

15 Claims, No Drawings

METHODS OF SCALE INHIBITION

This application is a continuation-in-part of copending application of Robert S. Mitchell, Ser. No. 361,838 filed May 17, 1973 and now abandoned.

BACKGROUND OF INVENTION

1. Field of the Invention

The present invention relates to methods of inhibiting the precipitation of metal ions from aqueous solutions, and to the use of certain phosphonomethylene amino carboxylates in such scale inhibition methods.

2. Description of Prior Art

Most commercial water contains iron and alkaline earth metal cations, such as calcium, barium, magnesium, etc., and several anions such as hydroxide, bicarbonate, carbonate, sulfate, oxalate, phosphate, silicate, fluoride, etc. When combinations of these anions and cations are present in concentrations which exceed the solubility of their reaction products under the conditions of use, precipitates form. For example, when the concentrations of calcium ion and sulfate ion exceed the solubility of the calcium sulfate, a solid phase of calcium sulfate will form. Solubility product concentrations are exceeded for various reasons, such as evaporation of the water phase, change in pH, pressure or temperature, and the introduction of additional ions which form insoluble compounds with the ions already present in the solution. As these reaction products precipitate on the surfaces of the water carrying system, they form scale. The scale prevents effective heat transfer, interferes with fluid flow, facilitates corrosive processes, and harbors bacteria. The presence of this scale is an expensive problem in many industrial water systems (e.g., boilers, cooling towers, evaporators, etc.), oilwells, and the like, causing delays and shutdowns for cleaning and removal. The prior art has not dealt with the preparation or use of phosphonomethylene amino $C_{3-15}$ alkylene carboxylates or aralkylene carboxylates which are the subject of the present invention. These carboxylates are effective metal ion sequestrants and are useful in water treatment for the inhibition of scale formation in aqueous systems, including scale inhibition by "threshold" quantities thereof.

SUMMARY

According to the present invention, it has been found that certain phosphonomethylene amino carboxylates corresponding to the following formula:

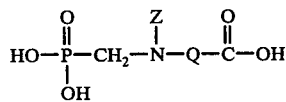

and salts and esters thereof wherein Q is an organic radical, as hereinafter defined, and Z is $-CH_2PO_3R_1R_2$ or an organic radical function as superior precipitation inhibitors when used in stoichiometric and substoichiometric amounts, including that phenomenon known in the art as the "threshold effect." These same compounds furthermore function as sequestering or chelating agents.

DESCRIPTION OF PREFERRED EMBODIMENTS

The phosphonomethylene amino carboxylates of the present invention as defined according to Formula I below may be prepared by reacting a cyclic amide with orthophosphorous acid (or $PCl_3$ and water) and formaldehyde, and are characterized by containing at least one N-C-P linkage derived from the cyclic amide - formaldehyde - phosphorous acid and at least one

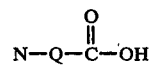

linkage derived from the cyclic amide. Many variations in specific structure of the compounds of Formula I are possible through variations in the structure of Z and Q. In general, Q may be any aliphatic or araliphatic radical available in the cyclic amide, and Z may be $-CH_2PO_3R_1R_2$ or any organic radical available in a nitrogen substituted cyclic amide.

Formula I includes esters, partial esters, salts, partial salts, acids and partial acids, and mixtures of such compounds, all of which are generically described and hereinafter referred to as "phosphonomethylene amino carboxylates" abbreviated as "PMAC."

Preferred phosphonomethylene amino carboxylates are those corresponding to the formula

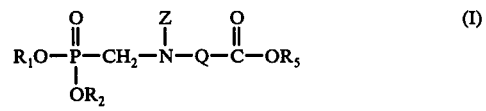

wherein $R_1$, $R_2$ and $R_5$ are individually selected from the group consisting of hydrogen, metal ions, ammonium ions, and alkyl ammonium ions, Z is $-CH_2PO_3R_1R_2$, $C_{1-4}$ alkyl or alkenyl, $C_{1-4}$ alkanol, $C_{1-4}$ alkyl carboxylic acid or a $C_{2-10}$ alkaminomethylene phosphonic acid radical, and Q is selected from the group consisting of $C_{3-15}$ alkylene and alkenylene radicals, and aralkylene radicals.

With respect to $R_1$, $R_2$ and $R_5$, useful metal ions include, for example, alkali metals such as sodium, lithium, and potassium; alkaline earth metals such as calcium and magnesium; aluminum, zinc, cadmium, manganese, nickel, cobalt, lead, tin, iron, chromium and copper. The preferred metal ions are those which produce a salt which is water-soluble in concentrations sufficient for the desired applications, the generally preferred metal ions being sodium, potassium and zinc. Where the metal ions are monovalent, each metal ion will replace an $R_1$, $R_2$ or $R_5$ on a 1 to 1 basis. Where the metal ions are divalent or trivalent, each metal ion will replace two or three R radicals respectively which may be any combination of $R_1$, $R_2$ and $R_5$ and may be from the same or different PMAC molecules.

Useful alkyl ammonium radicals are those derived from amines having a molecular weight below about 300, and more particularly from alkyl amines, alkylene diamines, and alkanol amines containing from 1 to about 10 carbon atoms and not more than two amine groups such as, for example, ethyl amine, diethyl amine, ethylene diamine, triethylamine, propyl amine, propylene diamine, hexyl amine, 2-ethylhexylamine N-butylethanol amine, triethanol amine, and the like.

Where Z is a $C_{2-10}$ alkaminomethylene phosphonic acid radical, useful radicals include those of the formula

wherein R is alkylene or alkenylene containing from 2 to about 10 carbon atoms and R' is —CH$_2$PO$_3$R$_1$R$_2$, C$_{1-4}$ alkyl, C$_{1-4}$ alkanol, or C$_{1-4}$ alkyl carboxylic acid.

With respect to Q, useful alkylene and alkenylene radicals are those containing 3 to about 15 carbon atoms and may be aliphatic or alicyclic, the alicyclic radicals usually containing from 4 to 10 carbon atoms. Useful aralkylene radicals are those containing 7 to about 14 carbon atoms, such as benzylene, xylylene and the like. The Q radicals may be unsubstituted or substituted with C$_{1-6}$ alkyl halogen, hydroxyl, or amine radicals wherein the halogen is chlorine, fluorine, or bromine.

The PMAC compounds useful in this invention alternatively can also be prepared by starting with the acyclic aminoalkanoic, alkenoic and aralkanoic acids which can be produced by hydrolysis of the cyclic amides described or other synthesis routes. The reaction of such acyclic amino acids with phosphorous acid and formaldehyde will produce the PMAC compounds useful in the present claimed method of inhibiting the precipitation of scale forming salts.

Representative examples of some PMAC compounds included within present invention are illustrated below:

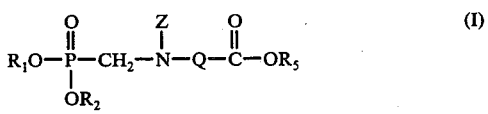
(I)

TABLE I

| Compound No. | R$_1$ | R$_2$ | R$_5$ | Q | Z |
|---|---|---|---|---|---|
| 1 | H | H | H | (CH$_2$)$_3$ | CH$_2$(PO$_3$H)$_2$ |
| 2 | " | " | " | (CH$_2$)$_5$ | " |
| 3 | " | " | " | (CH$_2$)$_7$ | " |
| 4 | " | " | " | (CH$_2$)$_{10}$ | " |
| 5 | " | " | " | (CH$_2$)$_{11}$ | " |
| 6 | " | " | " | (CH$_2$)$_{12}$ | " |
| 7 | " | " | C$_2$H$_5$NH$_3$ | (CH$_2$)$_5$ | " |
| 8 | " | " | H | (CH$_3$CCH$_3$)$_5$ | " |
| 9 | " | " | C$_2$H$_5$NH$_3$ | (CH$_2$)$_3$ | " |
| 10 | " | " | H | C$_6$H$_{10}$ | " |
| 11 | " | " | " | CH$_2$C$_6$H$_4$ | " |
| 12 | Na | " | Na | (CH$_2$)$_5$ | " |
| 13 | Zn | " | Zn | " | " |
| 14 | NH$_4$ | " | NH$_4$ | " | " |
| 15 | Na | Na | Na | (CH$_2$)$_3$ | " |
| 16 | K | K | K | " | " |
| 17 | NH$_4$ | NH$_4$ | NH$_4$ | " | " |
| 18 | C$_2$H$_5$NH$_3$ | C$_2$H$_5$NH$_3$ | H | (CH$_2$)$_5$ | " |
| 19 | H | H | H | (CH$_2$)$_3$ | (CH$_2$)$_3$N(CH$_2$PO$_3$H)$_2$ |
| 20 | " | " | " | " | (CH$_2$)$_3$N(CH$_2$COOH)-(CH$_2$PO$_3$H$_2$) |
| 21 | " | " | " | " | (CH$_2$)$_3$N(CH$_2$CH$_2$OH)(CH$_2$PO$_3$H$_2$) |
| 22 | " | " | " | (CH$_2$)$_5$ | (CH$_2$)$_2$N(CH$_2$COOH)$_2$ |
| 23 | " | " | " | " | (CH$_2$)$_2$N(CH$_2$CH$_2$OH)$_2$ |

In general, the PMAC compunds are prepared by reacting together
a. a phosphorous containing material which is orthophosphorous acid or a combination of PCl$_3$ and H$_2$O,
b. formaldehyde, and
c. a cyclic amide having the general formula

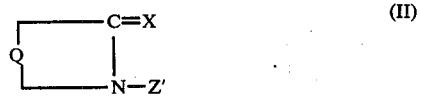
(II)

wherein X is oxygen or sulfur, Q is as defined in Formula I, and Z' is hydrogen, C$_{1-4}$ alkyl or alkenyl, C$_{1-4}$ alkanol, C$_{1-4}$ alkyl carboxylic acid, or a C$_{2-10}$ alkamino radical of the formula -RN(H)R" wherein R is as above defined and R" is hydrogen or R' as above defined.

The compounds falling within Formula II above are designated herein as "cyclic amides" and are to be distinguished from the alkyl ammonium ions, amines and PMAC. Cyclic amides falling within Formula II may be conveniently prepared according to the processes outlined in (1) "Advanced Organic Chemistry: Reactions, Mechanisms and Structure," Jerry March, 1968 by McGraw-Hill Book Company, New York; pages 337-819 and 820; and (2) "Chemistry of Organic Compounds, " C. R. Noller, 1951 by W. B. Saunders Company, Philadelphia, Pa.; page 722. Cyclic amides are also available commercially and the preparation of these compounds does not constitute part of the instant invention. It is to be understood that the amides falling within Formula II can be used in their technical grade form, chemically pure form, or crude form which is obtained directly from the synthesis of the cyclic amide.

Representative examples of cyclic amides included within Formula II are illustrated below:

2-pyrrolidone(butyrolactam) (III)

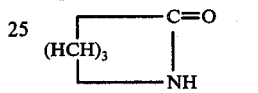

2-piperidone(valerolactam) (IV)

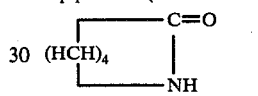

ε-caprolactam (V)

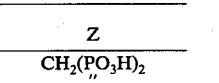

dodecyllactam (VI)

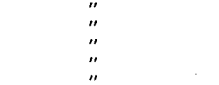

[2.2.2.]-bicyclohexyl-2-azaoctan-2-one (VII)

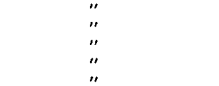

3,4-benzpyrrolidone (VIII)

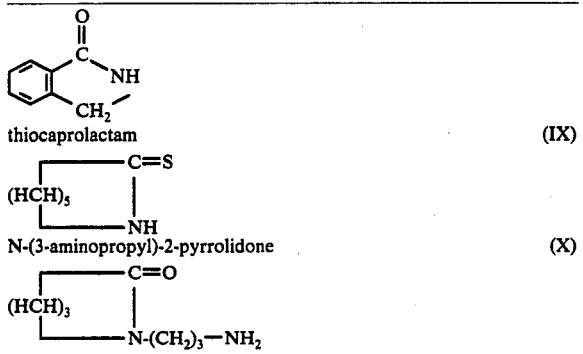

thiocaprolactam (IX)

N-(3-aminopropyl)-2-pyrrolidone (X)

When thiolactams such as that of Formula IX are utilized in the process of this invention, the sulfur atom is replaced by an oxygen during the reaction, and the reaction product is a PMAC compound corresponding to the structure given in Formula I above. For ease of description, the remainder of the application will refer to lactams as the cyclic amide reactant with the understanding that a corresponding thiolactam may be substituted therefor with equivalent results.

Particularly preferred cyclic amides are the lactams having the general formula (XI)

wherein $n$ is from about 3 to 11, with $\epsilon$-caprolactam (V) being particularly preferred as a readily available low cost reactant useful in the preparation of bis(phosphonomethyl)aminopentamethylene carboxylic acids and salts thereof useful in the method of the present invention.

The formaldehyde (or paraformaldehyde) used to prepare PMAC compounds useful in the practice of the present invention can be used per se or mixed with alcohols and/or water in order to facilitate easier handling of the reaction mass, temperature control and the prevention of foaming. For example, Formalin, which is a trademark for a 37% (United States) or 40% (British) formaldehye solution, is an aqueous solution generally containing from about 0% to about 40% methanol.

The preferred phosphorous containing compound for use to prepare PMAC compounds useful in the present invention is orthophosphorous acid which is commercially available. It is understood, however, that while $H_3PO_3$ is generally preferred, the individual ingredients $PCl_3$ and $H_2O$ which react to make orthophosphorous acid can be used separately and even added at different points of the manufacturing process.

Orthophosphorous acid can be utilized in the process of preparing PMAC compounds either as the acid per se or in the form of one of its salts such as its mono- or diammonium salts or its mono- or dialkaline metal salts. Such orthophosphorous acid salts will generally be utilized in combination with an amount of a supplementary acid sufficient to maintain the pH of the reaction mixture below about 4 and to convert the orthophosphorous acid salt into the more reactive acid form. The supplementary acid may be any strong acid as for example hydrochloric, sulfuric, hydrobromic, phosphoric, or sulfonic acid. For ease of description, the remainder of the specification will generally refer to orthophosphorous acid as the preferred phosphorous containing reactant.

The PMAC compounds of the present invention are prepared by reacting orthophosphorous acid, formaldehyde and a cyclic amide of Formula II in an aqueous mixture at elevated temperatures. The reaction mixture preferably contains from about 5 to 75 percent water, and most preferably from about 30 to 50 percent water promote the reaction and facilitate mixing, handling, and heat transfer. The rate of reaction increases with increasing temperature and the reaction temperature is preferably maintained above about 85° C. and most preferably at about reaction reflux temperature. Temperatures up to about 200° C. may be employed but temperatures in excess of 200° C. should be avoided to prevent decomposition of the orthophosphorous acid.

The pH of the reaction affects the rate of the desired reaction and the formation of by-product materials. The pH is preferably maintained below about 4 and most preferably below about 2 to maximize the formation of PMAC and to minimize the oxidation of phosphorous acid to phosphoric acid. The pH of the reaction medium is readily adjusted by the addition of hydrochloric acid or other strong mineral acid including for example sulfuric, sulfonic, hydrobromic and phosphoric acid.

The reaction preferably employs a catalytic amount of a halide ion to inhibit the oxidation of the orthophosphorous acid and to improve yields of reaction products. Although any halide ion may be used, chloride ion is preferred for economic reasons. Hydrochloric acid is a convenient source of chloride ion and serves the dual function of reducing the pH of the reaction mixture. The halide ion is preferably present in amounts of from about 0.01 to 10 percent by weight and most preferably in an amount of from 0.5 to about 3 percent by weight.

Catalysts which may be used in place of the preferred chloride ion include other halides, i.e., fluoride, bromide and iodide ions as well as sulfate, cyanide, borate, carbonate and sulfite ions. These ions may be supplied in the form of their acids or salts.

The reaction time and the sequence of addition of reactants is important to the operation of the process for preparing PMAC compounds. Although some PMAC reaction product will be obtained if all the reactants are simply combined and maintained at the desired pH and temperature for a period of from about 1 to 7 hours or longer, such a method results in the formation of considerable amounts of by-products and results in relatively low yields of PMAC.

In a preferred embodiment of the process the orthophosphorous acid and the cyclic amide are combined in a ratio of at least two moles of orthophosphorous acid for each mole of cyclic amide, and an excess of orthophosphorous acid may be used. These reactants are heated to the reaction temperature of at least about 85° C., preferably to the refluxing temperature of the mixture, and are preferably maintained at this temperature for an initial period of from about 10 minutes to about 5 hours or more, for instance from about 1 to 3 hours. Following this induction period the formaldehyde is slowly metered into the reaction media over a period of from about 10 minutes to about 3 hours with stirring and while maintaining the pH and temperature at reaction conditions. An addition of at least two moles formaldehye per mole of cyclic amide should be made and a molar excess of formaldehyde may be used.

Following the completion of the formaldehyde addition the reactants are maintained at reaction temperature, preferably at reflux for a period of time of from about 10 minutes to two hours or more to allow the reaction to proceed to maximum completion.

Side reactions occurring in the preparation of PMAC compounds are believed to include the oxidation of orthophosphorous acid to orthophosphoric acid and the formation of hydroxymethylene phosphonic acid. While the reaction product may be refined to remove these secondary products, in most instances their presence in the PMAC is not detrimental to its use in water treatment applications and purification of the product is not necessary. The loss of orthophosphorous acid and formaldehyde due to these side reactions may be compensated for by simply adding a slight excess of the stoichiometric amounts to these materials required for the desired reaction.

The reaction is described in the preparation of the acid form of the PMAC compounds. Salt forms are easily prepared by reacting such acids with a base which may be a metal hydroxide or an ammonium compound. The acid and salt forms of the PMAC compounds have utility in the field of treating water or aqueous systems and function as both a sequestering agent and as a "threshold" agent. Sequestration is accomplished by adding at least a stoichiometric amount of the PMAC compound as required to complex the metal ions present in the system. When using stoichiometric quantities the preferred mole ratio in from about 1:1 to 2.5:1 relative to the metal ions present. The term "threshold" as utilized herein refers to the chemical and/or physical phenomenon that less than stoichiometric quantities of the particular PMAC can effectively prevent the precipitation and/or alter the crystal forms of various salts of metallic ions such as calcium, iron, copper and cobalt. In other words, the "threshold" treatment of water is that technique by means of which usually from about 0.05 to 500 ppm and preferably from about 0.5 to 25 ppm, i.e., less than stoichiometric quantities of the treating agent, are added to the aqueous system to interfere with the growth of crystal nuclei and thereby prevent the deposition of insoluble deposits. When using such substoichiometric amounts, the preferred mole ratio of inhibitor to scale forming cations is from about 1:1.5 to 1:10,000. The term "threshold" is discussed in publications such as U.S. Pat. No. 2,038,316 and the articles by Reitmeier and Buehrer in the Journal of Physical Chemistry, Vol. 44, pages 535 to 574 (1939). An additional explanation of the threshold effect will be found in the publications of Hatch and Rice appearing in Industrial Engineering and Chemistry of January, 1939, and August, 1945.

It is within the scope of the present invention that the PMAC inhibitors of the present invention may also be used in aqueous systems which contain inorganic and/or organic materials (particularly, all ingredients or substances used by the water-treating industry), with the proviso that such materials do not render the PMAC compound substantially ineffective for its end purpose. These organic and inorganic materials, include, without limitation, polyacrylates, particularly those whose molecular weights are from about 2000 to about 20,000 and from about 20,000 to about 960,000, including water soluble polymers such as polyacrylic acid, polyacrylamide, partially hydrolyzed acrylamide and the like; tannins; lignins; deaerating materials; polymeric anhydrides (such as polymaleic anhydride); and sulfonated lignins. Other materials which can be used with said inhibitors include, for example, surface active agents, antifoam agents, acetodiphosphonic acids, inorganic phosphates including orthophosphates, molecularly dehydrated phosphates and phosphonates, polyfunctional phosphated polyol esters, calcium and magnesium salts such as calcium or magnesium chlorides sulfates, nitrates and bicarbonates and inorganic silicates. Furthermore, other scale and precipitation inhibitors such as amino tri-(methylene phosphonic acid) may be used in combination with the PMAC inhibitors of the present invention. For exemplary purposes only, these other precipitation inhibitors are described in U.S. Pat. Nos. 3,234,124; 3,336,221; 3,393,150; 3,400,078; 3,400,148; 3,434,969; 3,451,939; 3,462,365; 3,480,083; 3,591,513; 3,597,352 and 3,644,205.

The following examples are included to illustrate the practice of the present invention and the advantages provided thereby but are not to be considered limiting. Unless otherwise specified, all parts are parts by weight and all temperatures are in degrees centigrade.

EXAMPLE I

Into a 500 milliliter flask equipped with a water condenser and dropping funnel are charged approximately 166 grams (1.0 moles) of 49.9% orthophosphorous acid containing 15.5 grams of HCl, and 58 grams of 36% hydrochloric acid. The total moles of HCl is 1.0. To the resultant mixture is added approximately 56.5 grams (0.5 moles) ε-caprolactam in its technical grade form. The reaction mass is then heated to the boiling point over a period of about 20 minutes to obtain a homogeneous, clear solution having a boiling point of approximately 112°–115° C.

The resultant clear solution in the flask is maintained at boiling for about one hour, and then over a period of approximately 2.5 hours, approximately 37 grams (1.1 moles) of paraformaldehyde is added. At the end of the 2.5 hour period, the reaction mixture, which is a clear solution, is held at boiling with reflux for an additional 60 minutes and then is cooled to 25° C. The solution is found to be clear with an amber color prior to crystallization which occurs upon cooling. After crystallization, the crystals are filtered off, washed with acetone and dried. One hundred twenty-four (124) grams of white crystals are obtained with a yield of 77.3% of theory based on the cyclic amide reacted. P$^{31}$ Nuclear Magnetic Resonance (NMR) spectra and elemental analysis show the white crystal product to have the following structural formula corresponding to Compound No. 2 of Table I:

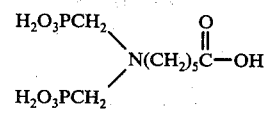

The specific elemental analysis for the product prepared by this Example I are as follows:

| Element | Theory, % | Found, % |
|---|---|---|
| Carbon (C) | 30.09 | 30.07 |
| Hydrogen (H) | 5.95 | 5.90 |
| Nitrogen (N) | 4.38 | 4.16 |
| Phosphorus (P) | 19.43 | 19.07 |
| P/N mole ratio | 2.00/1.00 | 2.03/1.00 |

The specific P$^{31}$ NMR ppm chemical shifts of the above product are as follows:

| ppm [1] | pH | Group Linkage |
|---|---|---|
| −10.7 | acid [2] | N-C-P |
| − 8.0 | Na salt [3] (alkaline) | N-C-P |

[1] One NMR resonance observed in spectrum at the shift indicated; no resonances observed for unreacted phosphorous acid.
[2] Product in acid solution prior to crystallization.
[3] Solution of the crystallized product in alkaline medium as sodium salt.

The NMR indicates that the reaction proceeded essentially to completion and that the 77.3% yield stated above could be increased upon refinement of the crystalline procedure used to obtain the remainder of product by procedures known to those skilled in the art.

EXAMPLE II

The procedure of Example I is repeated substituting 0.5 moles (65 grams) of thiocaprolactam for the ε-caprolactam of Example I. One hundred twenty two (122) grams of white crystals are obtained for a yield of about 76% of theory based upon the thiocaprolactam.

The P$^{31}$ NMR spectra and elemental analysis confirms the structure of the product to be the same as that obtained in Example I, that is corresponding to Compound No. 2 of Table I. Specific elemental analysis is as follows:

| Element | Theory, % | Found, % |
|---|---|---|
| Carbon (C) | 30.09 | 29.84 |
| Hydrogen (H) | 5.95 | 6.19 |
| Nitrogen (N) | 4.38 | 3.17 |
| Phosphorus (P) | 19.43 | 19.37 |
| P/N mole ratio | 2.00/100 | 2.42/1.00 |
| Sulfur | — | <0.1 |

EXAMPLE III

The procedure of Example I is repeated substituting 0.5 moles (43 grams) of 2-pyrrolidone for the ε-caprolactam of Example I. One hundred fourteen (114) grams of white crystals are obtained for a yield of 78.4% of theory based upon the 2-pyrrolidone. The p$^{31}$ NMR spectra and elemental analysis confirm the product to have the following structural formula corresponding to Compond No. 1 of Table I:

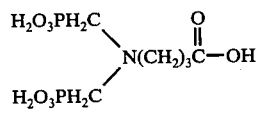

The specific elemental analysis for the product prepared by this Example are as follows:

| Element | Theory, % | Found, % |
|---|---|---|
| Carbon (C) | 24.75 | 24.64 |
| Hydrogen (H) | 5.19 | 5.32 |
| Nitrogen (N) | 4.81 | 5.32 |
| Phosphorus (P) | 21.28 | 21.22 |

The specific P$^{31}$ NMR ppm chemical shifts of the above product are as follows:

| ppm | pH | Group Linkage |
|---|---|---|
| −10.5 | acid | N-C-P |
| − 7.0 | K salt (alkaline) | N-C-P |

EXAMPLE IV

The procedure of Example I is repeated substituting 0.5 moles (99 grams) of dodecyllactam for the ε-caprolactam of Example I. Forty-eight (48) grams of fine white crystals are obtained for a yield of 23.8% of theory based upon the dodecyllactam. The P$^{31}$ NMR spectra and elemental analysis confirm the product to have the following structural formula corresponding to Compound No. 5 of Table I.

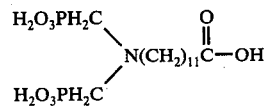

The specific elemental analysis for the product prepared by this Example are as follows:

| Element | Theory, % | Found, % |
|---|---|---|
| Carbon (C) | 41.69 | 41.96 |
| Hydrogen (H) | 7.69 | 7.83 |
| Nitrogen (N) | 3.47 | 3.47 |
| Phosphorus (P) | 15.38 | 14.91 |

The specific P$^{31}$ NMR ppm chemical shift of the above product is as follows:

| ppm | pH | Group Linkage |
|---|---|---|
| −6.0 | NH$_4$salt (alkaline) | N-C-P |

EXAMPLE V

Into a 250 milliliter flask equipped with a water condenser and dropping funnel are charged approximately 39.5 grams (0.24 moles) of 49.9% orthophosphorous acid containing 3.75 grams of HCl and 14.5 grams of 36% hydrochloric acid. The total moles of HCl is 0.24. To the resultant mixture is added approximately 15 grams (0.12 moles) of [2.2.2]-bicyclo-2-azaoctan-2-one. The reaction mass is then heated for about 30 minutes to bring it up to boiling, thereby obtaining a homogeneous, clear solution having a boiling point of approximately 110°–115° C.

The resultant clear solution in the flask is maintained at boiling for about 4 hours, and then over a period of approximately 60 minutes, approximately 8.7 grams (0.26 moles) of paraformaldehye is added. At the end of the 60 minute period, the reaction mixture, which is a clear to yellow-amber solution, is held at boiling reflux for an additional 30 minutes and then is cooled to about 25°–30° C. At 25°–30° C., the product is a slightly viscous yellow solution which does not crystallize at room temperature. The P$^{31}$ NMR spectra shows a typical ppm chemical shift resonance peak for N-C-P linkage as follows:

| ppm | pH | Group Linkage |
|---|---|---|
| −11.5 | acid | N-C-P |

The analysis indicates the reaction product has the following structural formula corresponding to Compound No. 1 of Table I:

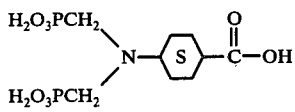

EXAMPLE VI

Into a 250 milliliter flask equipped with a water condenser and a dropping funnel are charged approximately 65.7 grams (0.40 moles) of 49.9% orthophosphorous acid containing 6.2 grams of HCl, and approximately 3.1 grams of 36% hydrochloric acid for a total of 7.3 grams (0.20 moles) of HCl. To the acid mixture is added 26.6 grams (0.20 moles) of 3,4-benzpyrrolidone and 25 milliliters of water. The mixture is heated with stirring and solution is obtained at 34° C. Heating is continued until reflux is obtained at approximately 108° C.

The solution is maintained at reflux for one hour and then over a period of about 2 hours there is slowly added 14.7 grams (0.44 moles) of 90% paraformalehyde. After addition of formaldehyde, the reaction mixture, which is a clear pale yellow solution, is held at reflux for an additional period of 6 hours. A sample taken for NMR analysis shows a typical ppm chemical shift at -9.3 and indicates that approximately 20% of the cyclic amide has been converted to PMAC Compound No. 11 of Table I having the following structural formula:

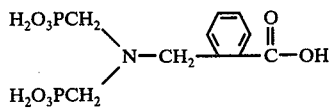

EXAMPLE VII

The procedure of Example I is repeated substituting 0.5 moles (71 grams) of N-(3-aminopropyl)-2-pyrrolidone for the ε-caprolactam of Example I. The reaction product is a yellow, viscous oily solution which does not crystallize at room temperature. The $P^{31}$ NMR spectra shows a typical ppm chemical shift resonance peak for N-C-P linkage as follows:

| ppm | pH | Group Linkage |
|---|---|---|
| −9.2 | acid | N-C-P |

The NMR spectra indicates approximately 80% conversion of cyclic amide to a compound having the following structural formula corresponding to Compound No. 19 of Table I:

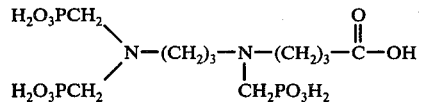

EXAMPLE VIII

In order to demonstrate the utility of the acids and salts of PMAC falling within Formula I above, the compounds prepared in Examples I to VII are evaluated for sequestration capability according to the procedure described in the book COORDINATION CHEMISTRY, "Calcium Complexing by Phosphorus Compounds," by C. F. Callis, A. F. Kerst and J. W. Lyons, pages 223–240, Plenum Press, 1969.

Approximately 1 gram of the PMAC to be evaluated is mixed with 0.1% by weight sodium oxalate in a 2-liter flask containing 100 milliliters of water. The pH is adjusted, if necessary to a pH of 11 by the addition of sodium hydroxide. Into the test solution there is titrated a 0.1 molar calcium nitrate solution via the use of a Sargent-Malmstadt automatic titrator, Model SE, and which also measures the turbidity by light transmission. The amount of calcium nitrate solution added is sufficient to determine the point of inflection at which the sequestrant-containing solution goes from a relatively clear solution to a turbid one. This inflection point is a measure of the amount of calcium sequestered by the PMAC compound.

The sequestration test demonstrates that the PMAC compounds of Examples I to VII are effective sequestering agents which are able to sequester from about 0.1 to 3 grams of calcium per 100 grams of PMAC compound. Equivalent results are obtained with other PMAC compounds corresponding to the acids and salts of Formula I.

EXAMPLE IX

The ability of PMAC compounds to act as threshold agents to inhibit precipitation of calcium sulfate over extended periods of time was determined by preparing a solution of 5 ppm inhibitor and 10,000 ppm calcium sulfate in deionized water, and adjusting the pH to 7.0 by the addition of NaOH. The prepared samples were placed on a shaker and continually agitated during the period of the test. Aliquots from duplicate samples were taken at designated intervals, and the calcium content remaining in solution determined by EDTA Eriochrome Black T titration of filtrate.

Compound No. 1 prepared according to Example II was evaluated in direct comparison with bis(phosphonomethylene) aminomethylene carboxylate of the prior art which had been suggested for certain uses in water treatment. Compound No. 1 was discovered to be surprisingly more effective as a threshold agent than the lower homologue of the prior art. The relative effectiveness of these two cpompounds is shown by the following data:

| Additive | % Calcium Remaining in Solution | | | | |
|---|---|---|---|---|---|
| | 5 hrs. | 1 day | 3 days | 8 days | 27 days |
| $N(CH_2PO_3H_2)_2CH_2COOH$ | 100 | 86 | 51 | 39 | — |
| $N(CH_2PO_3H_2)_2(CH_2)_3COOH$ | 100 | 100 | 100 | 100 | 34 |

EXAMPLE X

The ability of PMAC compounds to act as threshold agents to inhibit precipitation of calcium sulfate at extremely low concentrations is demonstrated by preparing solutions of 10, 4, 2, 1, and 0.5 ppm inhibitor and 10,000 ppm calcium sulfate in deionized water, and adjusting the pH to 7.0 by the addition of NaOH. The prepared samples are placed on a shaker and continually agigated during the period of the test. Aliquots from duplicate samples are taken at designated intervals, and the calcium content remaining in solution determined by EDTA Eriochrome Black T titration of filtrate. The percent of calcium remaining in solution is compared to the percent of calcium remaining in an uninhibited solution (Blank).

In the manner outlined above Compound Nos. 1, 2 and 11 from TABLE I are evaluated against blank solutions of 10,000 ppm of calcium sulfate in deionized water at 10, 4, 2, 1 and 0.5 ppm of each inhibitor. All the PMAC compounds were found to be effective as threshold agents in preventing calcium sulfate scale as shown by the following data taken after 24 hours on test:

TABLE II

| Additive, ppm | % Calcium Remaining in Solution | | | | |
|---|---|---|---|---|---|
| | 10 | 4 | 2 | 1 | 0.5 |
| $N(CH_2PO_3H_2)_2(CH_2)_3COOH$ | 100 | 100 | 92.7 | 67.8 | 56.0 |
| Blank | 41.5 | — | — | — | — |
| $N(CH_2PO_3H_2)_2(CH_2)_5COOH$ | 96 | 97.2 | 91.6 | 40.9 | 37.2 |
| Blank | 33.6 | — | — | — | — |
| $N(CH_2PO_3H_2)_2CH_2C_6H_4COOH$ | 99.3 | 99.3 | 59.3 | 36.0 | 32.6 |
| Blank | 32.6 | — | — | — | — |

Comparable results in threshold inhibition of calcium sulfate precipitation are also obtained with the other PVPAC acids and salts described herein, and those compounds are useful to prevent scale formation in aqueous systems such as cooling towers.

The above examples have been described in the foregoing specifications for the purpose of illustration and not limitation. Many other modifications and ramifications will naturally suggest themselves to those skilled in the art based on this disclosure. These are intended to be comprehended as within the scope of this invention.

What is claimed is:

1. A method of inhibiting the precipitation of scale forming salts in an aqueous system comprising adding to said system at least a precipitation inhibiting amount of a phosphonomethylene amino carboxylate having the general formula $$R_1O-\overset{\overset{O}{\|}}{\underset{\underset{OR_2}{|}}{P}}-CH_2-\overset{\overset{Z}{|}}{N}-Q-\overset{\overset{O}{\|}}{C}-OR_5$$

wherein $R_1$, $R_2$ and $R_5$ are individually selected from the group consisting of hydrogen, alkali and alkaline earth metal ions, ammonium ions and alkyl ammonium ions containing up to about 18 carbon atoms; Z is selected from the group consisting of $-CH_2PO_3R_1R_2$, $C_{1-4}$ alkyl, $C_{1-4}$ alkenyl, $C_{1-4}$ alkanol, $C_{1-4}$ alkyl carboxylic acid, and $C_{2-10}$ alkaminomethylene phosphonic acid; and Q is selected from the group consisting of $C_{3-15}$ alkylene and alkenylene radicals and $C_{7-14}$ alkaryl radicals.

2. The method of claim 1 wherein the scale forming salt is an alkaline earth metal carbonate, sulfate, oxalate, phosphate, fluoride or silicate.

3. The method of claim 1 wherein the mole ratio of precipitation inhibitor to scale forming salts is from about 1 to 1.5 to about 1 to 10,000.

4. The method of claim 1 wherein the precipitation inhibitor is present in the system at a concentration of from about 0.05 to about 500 parts per million.

5. The method of claim 1 wherein each of $R_1$, $R_2$ and $R_5$ is hydrogen.

6. The method of claim 1 wherein said carboxylate is an alkali metal salt.

7. The method of claim 1 wherein said carboxylate is an ammonium salt.

8. The method of claim 1 wherein each of $R_1$ and $R_5$ is an alkali metal ion and each $R_2$ is hydrogen.

9. The method of claim 1 wherein each of $R_1$ and $R_5$ is an ammonium ion and each $R_2$ is hydrogen.

10. The method of claim 1 wherein Q is a $C_{3-11}$ alkylene radical.

11. The method of claim 1 wherein said carboxylate is bis(phosphonomethylene)aminopropylene carboxylic acid.

12. The method of claim 1 wherein said carboxylate is bis(phosphonomethylene)aminopentylene carboxylic acid.

13. The method of claim 1 wherein said carboxylate is bis(phosphonomethylene)aminobenzylene carboxylic acid.

14. The method of claim 1 wherein the aqueous system contains an inorganic polyphosphate.

15. The method of claim 1 wherein the aqueous system contains a water-soluble polyacrylate.

* * * * *

UNITED STATES PATENT AND TRADEMARK OFFICE
CERTIFICATE OF CORRECTION

PATENT NO. : 4,079,006
DATED : March 14, 1978
INVENTOR(S) : Robert S. Mitchell

It is certified that error appears in the above-identified patent and that said Letters Patent are hereby corrected as shown below:

Column 1, line 5, "361,838" should be corrected to read -- 361,383 --.

Table I, in the column headings, "O" should be corrected to read -- Q --.

Column 11, line 10, "No. 1" should be corrected to read -- No. 10 --.

Signed and Sealed this

Twenty-seventh Day of June 1978

[SEAL]

Attest:

RUTH C. MASON
Attesting Officer

DONALD W. BANNER
Commissioner of Patents and Trademarks